(12) United States Patent
Foster (10) Patent No.: US 11,965,879 B2
(45) Date of Patent: Apr. 23, 2024

(54) METHOD FOR DIAGNOSING AND ASSESSING ENDOMETRIOSIS

(71) Applicant: McMaster University, Hamilton (CA)

(72) Inventor: Warren G Foster, Hamilton (CA)

(73) Assignee: McMaster University, Hamilton (CA)

( * ) Notice: Subject to any disclaimer, the term of this patent is extended or adjusted under 35 U.S.C. 154(b) by 532 days.

(21) Appl. No.: 16/999,851

(22) Filed: Aug. 21, 2020

(65) Prior Publication Data

US 2021/0123910 A1 Apr. 29, 2021

Related U.S. Application Data

(60) Provisional application No. 62/890,896, filed on Aug. 23, 2019.

(51) Int. Cl.
*A61K 45/06* (2006.01)
*C12Q 1/6837* (2018.01)
*G01N 33/53* (2006.01)

(52) U.S. Cl.
CPC ......... *G01N 33/5308* (2013.01); *A61K 45/06* (2013.01); *C12Q 1/6837* (2013.01); *B01J 2219/00529* (2013.01); *G01N 2496/00* (2013.01); *G01N 2800/364* (2013.01)

(58) Field of Classification Search
None
See application file for complete search history.

(56) References Cited

U.S. PATENT DOCUMENTS

| | | |
|---|---|---|
| 2017/0175190 A1 | 6/2017 | Taylor et al. |
| 2019/0233892 A1 | 8/2019 | Cotter et al. |
| 2019/0276893 A1 | 9/2019 | Taylor |

FOREIGN PATENT DOCUMENTS

GB  WO 2017153710  * 9/2017  ............... C12Q 1/68

OTHER PUBLICATIONS

Cho et al., Am. J. Reprod. Immunol. 2007, 58, 497-504 (Year: 2007).*
Rao et al., Biostat Bioinforma Biomath. Author manuscript; available in PMC Dec. 31, 2014; 13 pages total (Year: 2014).*
Papari et al., Fertil Steril 2020; 113: 1232-41 (Year: 2020).*
Onrat et al., Genetic Testing and Molecular Biomarkers, 2018; 22: 644-651; doi: 10.1089/gtmb.2018.0188 (Year: 2018).*
Masè et al. (2017) Sci. Rep. 7, 41127; doi: 10.1038/srep41127 (Year: 2017).*
Veryaskina et al., PLOS ONE 17(2): e0254304, https://doi.org/10.1371/journal.pone.0254304 (Year: 2022).*
Agarwal SK, Chapron C, Giudice LC, Laufer MR, Leyland N, Missmer SA, Singh SS, and Taylor HS. Clinical diagnosis of endometriosis: a call to action. Am J Obstet Gynecol 2019: 220; 354.e351-354.e312. Bartel DP. MicroRNAs: genomics, biogenesis, mechanism, and function. Cell 2004: 116; 281-297.
Bartel DP. MicroRNAs: target recognition and regulatory functions. cell 2009: 136; 215-233. Bashti O, Noruzinia M, Garshasbi M, and Abtahi M. miR-31 and miR-145 as Potential Non-Invasive Regulatory Biomarkers in Patients with Endometriosis. Cell J 2018: 20; 293.
Bockaj M, Fung B, Tsoulis M, Foster WG, and Soleymani L. Method for Electrochemical Detection of Brain Derived Neurotrophic Factor (BDNF) in Plasma. Anal Chem 2018: 90; 8561-8566.
Burney RO and Giudice LC. Pathogenesis and pathophysiology of endometriosis. Fertility and sterility 2012: 98; 511-519.
Cho S, Mutlu L, Grechukhina O, and Taylor HS. Circulating microRNAs as potential biomarkers for endometriosis. Fertil Steril 2015: 103; 1252-1260 e1251.
Cosar E, Mamillapalli R, Ersoy GS, Cho S, Seifer B, and Taylor HS. Serum microRNAs as diagnostic markers of endometriosis: a comprehensive array-based analysis. Fertil Steril 2016.
Fadhlaoui A, Gillon T, Lebbi I, Bouquet de Jolinière J, and Feki A. Endometriosis and vesico-sphincteral disorders. Frontiers in surgery 2015: 2; 23.
Fassbender A, Burney RO, O DF, D'Hooghe T, and Giudice L. Update on Biomarkers for the Detection of Endometriosis. Biomed Res Int 2015: 2015; 130854.
Fuldeore M, Yang H, Du EX, Soliman AM, Wu EQ, and Winkel C. Healthcare utilization and costs in women diagnosed with endometriosis before and after diagnosis: a longitudinal analysis of claims databases. Fertility and sterility 2015: 103; 163-171. Giudice LC. Endometriosis. New England Journal of Medicine 2010: 362; 2389-2398.
Jia S-z, Yang Y, Lang J, Sun P, and Leng J. Plasma miR-17-5p, miR-20a and miR-22 are down-regulated in women with endometriosis. Human reproduction 2012: 28; 322-330.
May KE, Conduit-Hulbert SA, Villar J, Kirtley S, Kennedy SH, and Becker CM. Peripheral biomarkers of endometriosis: a systematic review. Hum.Reprod. Update. 2010: 16; 651-674.
May KE, Villar J, Kirtley S, Kennedy SH, and Becker CM. Endometrial alterations in endometriosis: a systematic review of putative biomarkers. Hum.Reprod.Update. 2011: 17; 637-653.
Nisenblat V, Bossuyt PM, Shaikh R, Farquhar C, Jordan V, Scheffers CS, Mol BW, Johnson N, and Hull ML. Blood biomarkers for the non-invasive diagnosis of endometriosis. Cochrane Database Syst Rev 2016: 5; CD012179.

(Continued)

Primary Examiner — Christina M Borgeest
(74) Attorney, Agent, or Firm — Gowling WLG (Canada) LLP (57) ABSTRACT

A method of detecting the expression level of miRNA markers in a biological sample obtained from a mammal is provided. The method incudes the steps of i) detecting the expression level of one or more miRNA markers selected from the group of miR-199a-3p, miR-143-3p, miR-340-5p, let-7b-5p, miR-21-5p, miR-17-5p, miR-20a-5p and miR-103a-3p, in the biological sample; ii) detecting the expression level of at least one miRNA reference marker selected from miR-148b-3p and miR-30e-5p in the biological sample; and iii) normalizing the expression level of the miRNA marker(s) against the expression level of the miRNA reference marker in the sample and in a control. The method is useful for the diagnosis of endometriosis, monitoring of patient response to treatment, and assessment of disease progression and/or severity.

17 Claims, 6 Drawing Sheets
Specification includes a Sequence Listing.

(56) References Cited

OTHER PUBLICATIONS

Nisenblat V, Sharkey DJ, Wang Z, Evans SF, Healey M, Ohlsson Teague EMC, Print CG, Robertson SA, and Hull ML. Plasma microRNAs display limited potential as diagnostic tools for endometriosis. J Clin Endocrinol Metab 2019.

Nnoaham KE, Hummelshoj L, Webster P, d'Hooghe T, de Cicco Nardone F, de Cicco Nardone C, Jenkinson C, Kennedy SH, Zondervan KT, and Study WERFG. Impact of endometriosis on quality of life and work productivity: a multicenter study across ten countries. Fertility and sterility 2011: 96; 366-373. e368.

Nothnick WB, Falcone T, Joshi N, Fazleabas AT, and Graham A. Serum miR-451a Levels Are Significantly Elevated in Women With Endometriosis and Recapitulated in Baboons (*Papio anubis*) With Experimentally-Induced Disease. Reprod Sci 2017: 24; 1195-1202.

Rekker K, Saare M, Roost AM, Kaart T, Soritsa D, Karro H, Soritsa A, Simon C, Salumets A, and Peters M. Circulating miR-200-family micro-RNAs have altered plasma levels in patients with endometriosis and vary with blood collection time. Fertil Steril 2015: 104; 938-946 e932.

Rogers PA, Adamson GD, Al-Jefout M, Becker CM, D'Hooghe TM, Dunselman GA, Fazleabas A, Giudice LC, Horne AW, Hull ML, et al. Research Priorities for Endometriosis. Reprod Sci 2017: 24; 202-226.

Shah DK, Correia KF, Vitonis AF, and Missmer SA. Body size and endometriosis: results from 20 years of follow-up within the Nurses' Health Study II prospective cohort. Hum.Reprod. 2013.

Sueta A, Yamamoto Y, Tomiguchi M, Takeshita T, Yamamoto-Ibusuki M, and Iwase H. Differential expression of exosomal miRNAs between breast cancer patients with and without recurrence. Oncotarget 2017: 8; 69934-69944.

Tamaresis JS, Irwin JC, Goldfien GA, Rabban JT, Burney RO, Nezhat C, DePaolo LV, and Giudice LC. Molecular classification of endometriosis and disease stage using high-dimensional genomic data. Endocrinology 2014: 155; 4986-4999.

Taylor HS, Adamson GD, Diamond MP, Goldstein SR, Horne AW, Missmer SA, Snabes MC, Surrey E, and Taylor RN. An evidence-based approach to assessing surgical versus clinical diagnosis of symptomatic endometriosis. Int J Gynaecol Obstet 2018: 142; 131-142.

Wang M, Gu H, Wang S, Qian H, Zhu W, Zhang L, Zhao C, Tao Y, and Xu W. Circulating miR-17-5p and miR-20a: molecular markers for gastric cancer. Molecular medicine reports 2012: 5; 1514-1520.

Wang W-T, Zhao Y-N, Han B-W, Hong S-J, and Chen Y-Q. Circulating microRNAs identified in a genome-wide serum microRNA expression analysis as noninvasive biomarkers for endometriosis. The Journal of Clinical Endocrinology & Metabolism 2013: 98; 281-289.

\* cited by examiner

SEQUENCE LISTING

```
<160> NUMBER OF SEQ ID NOS: 10

<210> SEQ ID NO 1
<211> LENGTH: 22
<212> TYPE: RNA
<213> ORGANISM: Homo sapiens

<400> SEQUENCE: 1
uuauaaagca augagacuga uu                                              22

<210> SEQ ID NO 2
<211> LENGTH: 22
<212> TYPE: RNA
<213> ORGANISM: Homo sapiens

<400> SEQUENCE: 2
ugagguagua gguugugugg uu                                              22

<210> SEQ ID NO 3
<211> LENGTH: 22
<212> TYPE: RNA
<213> ORGANISM: Homo sapiens

<400> SEQUENCE: 3
uagcuuauca gacugauguu ga                                              22

<210> SEQ ID NO 4
<211> LENGTH: 23
<212> TYPE: RNA
<213> ORGANISM: Homo sapiens

<400> SEQUENCE: 4
caaagugcuu acagugcagg uag                                             23

<210> SEQ ID NO 5
<211> LENGTH: 23
<212> TYPE: RNA
<213> ORGANISM: Homo sapiens

<400> SEQUENCE: 5
uaaagugcuu auagugcagg uag                                             23

<210> SEQ ID NO 6
<211> LENGTH: 23
<212> TYPE: RNA
<213> ORGANISM: Homo sapiens

<400> SEQUENCE: 6
agcagcauug uacagggcua uga                                             23
```

```
<210> SEQ ID NO 7
<211> LENGTH: 22
<212> TYPE: RNA
<213> ORGANISM: Homo sapiens

<400> SEQUENCE: 7
acaguagucu gcacauuggu ua                                            22

<210> SEQ ID NO 8
<211> LENGTH: 21
<212> TYPE: RNA
<213> ORGANISM: Homo sapiens

<400> SEQUENCE: 8
ugagaugaag cacuguagcu c                                             21

<210> SEQ ID NO 9
<211> LENGTH: 22
<212> TYPE: RNA
<213> ORGANISM: Homo sapiens

<400> SEQUENCE: 9
ucagugcauc acagaacuuu gu                                            22

<210> SEQ ID NO 10
<211> LENGTH: 21
<212> TYPE: RNA
<213> ORGANISM: Homo sapiens

<400> SEQUENCE: 10
uguaaacauc cuugacugga a                                             21
```

METHOD FOR DIAGNOSING AND ASSESSING ENDOMETRIOSIS

FIELD OF INVENTION

The present invention generally relates to methods for detecting miRNA in a biological sample, and more particularly relates to methods useful in the diagnosis of gynecological disorders, in particular, endometriosis.

BACKGROUND OF THE INVENTION

Endometriosis is a common chronic and benign, estrogen dependent gynecological disorder with a prevalence of 1-10% of women of reproductive age and 35-50% of women with infertility and pelvic pain (Giudice 2010; Tamaresis et al. 2014; Burney and Giudice 2012). Endometriosis is characterized by pain and infertility arising from the growth of endometrial stromal cells and glands outside the uterine cavity (Giudice 2010). The lack of a diagnostic blood test leads to diagnostic delays of on average 7 years (Nnoaham et al. 2011; Fuldeore et al. 2015) with laparoscopy, either alone or in combination with histopathological evidence of endometrial stroma and glands, remaining the gold standard for the diagnosis of endometriosis (Fadhlaoui et al. 2015). Laparoscopy is an expensive and invasiveness procedure whose risks, although rare, are serious. Consequently, diagnostic markers of endometriosis have been sought to provide more timely access to appropriate effective treatment alternatives for endometriosis. However, no clinical marker of endometriosis, either alone or in combination, has provided adequate sensitivity or specificity for the diagnosis of endometriosis (May et al. 2010; May et al. 2011; Fassbender et al. 2015; Nisenblat et al. 2016). Thus, the search for suitable diagnostic markers of endometriosis remains a high but unmet research priority (Rogers et al. 2017).

Recently, several groups (Cosar et al. 2016; Cho et al. 2015; Wang et al. 2013; Jia et al. 2013; Nothnick et al. 2017; Rekker et al. 2015; Bashti et al. 2018; Nisenblat et al. 2019) have explored the potential of circulating microRNA (miRNA) levels for the diagnosis of endometriosis. miRNAs are single stranded RNA that are 21-25 nucleotides in length, which act as post transcriptional silencers of gene expression by degradation of their target RNAs (Bartel 2004). miRNA are present in body fluids including blood, either contained in exosomes or bound to protein complexes which makes them more stable than circulating hormone or cytokine concentrations and therefore better candidate markers of a diseases (Shah et al. 2013). One miRNA can target several genes, or one gene can be targeted by different miRNAs (Bartel 2009). Circulating levels of miRNAs are dysregulated in several different cancers (Jia et al. 2012; Wang et al. 2012; Sueta et al. 2017) and endometriosis (Cosar et al. 2016; Cho et al. 2015; Wang et al. 2013; Jia et al. 2013; Nothnick et al. 2017; Rekker et al. 2015; Bashti et al. 2018; Nisenblat et al. 2019). While circulating levels of multiple miRNA differed significantly between women with endometriosis compared to controls, the results have largely not been reproduceable, and thus, miRNA appears to have limited potential for use as diagnostic markers of endometriosis (Nisenblat et al. 2019). However, prior studies suffer from the use of unvalidated reference material to normalize results, and failure to control for hemolysis (a factor known to adversely affect the reliability of results). Consequently, the potential of miRNA for effective diagnosis of endometriosis remains unresolved.

Diagnostic delay, cost, surgical risk, and poor correlation between symptoms and extent of disease are the basis for arguments to shift from surgical to clinical diagnosis (Agarwal et al. 2019; Taylor et al. 2018). Thus, there remains an uregent and unmet need for methods suitable to replace laparoscopy as the diagnostic standard for endometriosis to reduce the number of women needing laparoscopy, permit earlier detection of endometriosis and enable women more timely access to effective treatment options that attenuate disease severity and complications. Moreover, reduced need for diagnostic laparoscopy will mitigate surgical risks and reduce the health care costs associated with caring for women with endometriosis.

SUMMARY OF THE INVENTION

The present application discloses methods and kits for detecting the level of specific miRNAs in a mammalian sample. The method is useful for the diagnosis of endometriosis, monitoring of patient response to treatment, and assessment of disease progression and/or severity.

Thus, in one aspect of the invention, a method of detecting the expression level of miRNA markers in a biological sample obtained from a mammal is provided, comprising:

i) detecting the expression level of one or more miRNA markers selected from the group of miR-199a-3p, miR-143-3p, miR-340-5p, let-7b-5p, miR-21-5p, miR-17-5p, miR-20a-5p and miR-103a-3p, in a biological sample obtained from the mammal;

ii) detecting the expression level of at least one miRNA reference marker selected from miR-148b-3p and hsa-miR-30e-5p in the biological sample obtained from the mammal; and iii) normalizing the expression level of the miRNA marker(s) against the expression level of the miRNA reference marker in the sample and in a control.

In another aspect of the invention, a method of diagnosing endometriosis in a mammal is provided comprising:

i) detecting the expression level of at least 3 miRNA markers selected from the group of miR-199a-3p, miR-143-3p, miR-340-5p, let-7b-5p, miR-21-5p, miR-17-5p, miR-20a-5p and miR-103a-3p, in a biological sample obtained from the mammal;

ii) detecting the expression level of an miRNA reference marker selected from miR-148b-3p and hsa-miR-30e-5p in the biological sample obtained from the mammal;

iii) normalizing the expression level of the miRNA markers based on the expression level of miRNA reference markers in the sample and in a control; and iv) diagnosing the mammal with endometriosis when the normalized expression levels of the miRNA markers are less than the expression level of the miRNA markers in the control.

In another aspect of the application, provided is a kit comprising primers for miRNA markers and controls, and optionally instructions for use in the method disclosed herein.

Other features and advantages of aspects and embodiments of the present invention will become apparent from the following detailed description and figures.

DETAILED DESCRIPTION OF THE INVENTION

In one aspect, a method of detecting the expression level of miRNA markers in a biological sample obtained from a mammal is provided, comprising: i) detecting the expression level of one or more miRNA markers selected from the group of miR-199a-3p, miR-143-3p, miR-340-5p, let-7b-5p, miR-21-5p, miR-17-5p, miR-20a-5p and miR-103a-3p, in a biological sample obtained from the mammal; ii) detecting the expression level of at least one miRNA reference marker selected from miR-148b-3p and hsa-miR-30e-5p in the biological sample obtained from the mammal; and iii) normalizing the expression level of the miRNA marker(s) against the expression level of the miRNA reference marker in the sample and in a control. The method has been determined to be useful to diagnose endometriosis in the mammal. The detection of lower expression levels of the miRNA markers as compared to the miRNA controls is indicative of endometriosis. In some embodiments, the miRNA markers are circulating miRNA.

The term "mammal" is used herein to refer to both human and non-human mammals including non-human primates and domestic animals, e.g. cats, dogs and the like, livestock and undomesticated animals.

The term "biological sample" as used herein is meant to encompass any mammalian fluid or tissue sample that may contain nucleic acids, such as miRNA. Suitable biological samples include, but are not limited to: saliva, tears, sweat, blood (including menses), serum, plasma, urine, peritoneal fluid, uterine fluid or biopsied endometrial tissue. Any of these samples may be obtained from the mammal in a manner well-established in the art.

The sequences of the miRNA markers to be detected in methods of the present invention are readily available from relevant sequence databases, e.g. NCBI and/or other sequence databases, including both human and corresponding non-human sequences.

To conduct the present method, a suitable biological sample(s) is obtained from a female mammal, and it is analyzed to determine the expression level of selected miRNA markers in the sample. As one of skill in the art will appreciate, the expression level of each biomarker may be determined using one of several techniques established in the art, including methods of quantifying nucleic acids, such as PCR-based techniques, microarrays, gene expression systems, and Northern or Southern blotting techniques.

In one embodiment, PCR-based techniques (such as RT-PCR), and Northern or Southern blotting techniques which generally include the application of gel electrophoresis to isolate the target nucleic acid, followed by hybridization with specific labeled nucleic acid probes or primers. Primers for use in these methods are designed based on the miRNA marker sequences to specifically bind with the target miRNA, and comprise a complementary sequence to a region of the target miRNA, or comprise a complementary sequence to the full-length miRNA. Preferred primer sequences for each miRNA marker comprise the following sequences:

```
miR-340-5p,
                                     (SEQ ID NO: 1)
uuauaaagcaaugagacugauu;

let-7b-5p,
                                     (SEQ ID NO: 2)
ugagguaguagguugugugguu;

miR-21-5p,
                                     (SEQ ID NO: 3)
uagcuuaucagacugauguuga;

miR-17-5p,
                                     (SEQ ID NO: 4)
caaagugcuuacagugcagguag;

miR-20a-5p,
                                     (SEQ ID NO: 5)
uaaagugcuuauagugcagguag;

miR-103a-3p,
                                     (SEQ ID NO: 6)
agcagcauuguacagggcuauga;

miR-199a-3p,
                                     (SEQ ID NO: 7)
acaguagucugcacauugguua;
and miR-143-3p,
                                     (SEQ ID NO: 8)
ugagaugaagcacuguagcuc.
```

Quantitative reverse transcription PCR (RT-qPCR) to detect expression levels of miRNA markers may comprise one or two steps. Generally, the method comprises transcribing of the RNA into complementary DNA (cDNA) by reverse transcriptase. The cDNA is then used as the template for the qPCR reaction. One-step assays combine reverse transcription and PCR in a single tube and buffer, using a reverse transcriptase along with a DNA polymerase, and sequence-specific PCR primers. In two-step assays, the reverse transcription and PCR steps are performed in separate tubes, with different optimized buffers, reaction conditions, and priming strategies.

Suitable labels for use are well-known, and include, for example, fluorescent, phosphorescent and luminescent (e.g. chemiluminescent or bioluminescent) compounds, dyes, particles such as colloidal gold chemiluminescent and radioactive labels.

The expression level of the selected miRNA markers in a given sample may be detected individually or together using, for example, biochip array technology. Generally, biochip arrays provide a means to simultaneously determine the level of multiple miRNA markers in a given sample. These arrays may utilize RT-PCR technology and, thus, the biochip may be modified to incorporate suitable primers.

Once the expression level of selected miRNA markers in a biological sample of a mammal has been determined, these expression levels are normalized based on the expression level of reference miRNAs, i.e. miRNAs that are not differentially expressed in mammals with endometriosis versus mammals without endometriosis (control), in both the sample and a control. As one of skill in the art will appreciate, control values may be of an individual mammal that does not have endometriosis, or more likely, will be based on the expression levels in a population that does not have endometriosis. In some embodiments, the reference miRNA is selected from hsa-miR-148b-3p and hsa-miR-30e-5p. In other embodiments, the reference miRNA is hsa-miR-148b-3p and hsa-miR-30e-5p.

The expression level of reference miRNAs is detected using the same methods used to detect the miRNA target sequences. PCR-based techniques (such as RT-PCR) are used in one embodiment using primers designed based on the miRNA marker sequences of the reference miRNA, including a complementary sequence to a region of the reference miRNA or to the full-length miRNA. Preferred primer sequences for each miRNA marker comprise the following sequences:

```
miR-148b-3p -
                         (SEQ ID NO: 9)
ucagugcaucacagaacuuugu miR-30e-5p -
                         (SEQ ID NO: 10)
uguaaacauccuugacuggaa
```

In a method of diagnosing endometriosis in a mammal, normalized expression levels of miRNA markers are compared to control expression levels of miRNA markers. A mammal is diagnosed with endometriosis when the expression levels of miRNA markers are detected and are less than the expression level of the miRNA marker control levels, e.g. at least about 10%, 20% 30%, 40% or 50% less than the expression level of the miRNA marker control expression levels.

Thus, a method of diagnosing endometriosis in a mammal is provided comprising: i) detecting the expression level of at least 3 miRNA markers selected from the group of miR-199a-3p, miR-143-3p, miR-340-5p, let-7b-5p, miR-21-5p, miR-17-5p, miR-20a-5p and miR-103a-3p, in a biological sample obtained from the mammal; ii) detecting the expression level of at least one miRNA reference markers selected from miR-148b-3p and hsa-miR-30e-5p in the biological sample obtained from the mammal; iii) normalize the expression level of the miRNA markers based on the expression level of miRNA reference markers in the sample and in a control; and iv) diagnosing the mammal with endometriosis when the normalized expression levels of the miRNA markers are less than the expression level of the miRNA markers in the control.

In another embodiment, the miRNA markers comprise miR-199a-3p, miR-143-3p, miR-340-5p, let-7b-5p, miR-21-5p, miR-17-5p, miR-20a-5p and miR-103a-3p. In one preferred embodiment, the miRNA markers comprise miR-17-5p, miR-20a-5p, miR-199a-3p, miR-143-3p, and let-7b-5p. In another preferred embodiment, the miRNA markers consist of miR-17-5p, miR-20a-5p, miR-199a-3p, miR-143-3p, and let-7b-5p.

The present invention also provides a method of diagnosing the stage or severity of endometriosis, including lesion analysis. The greater the decrease in the expression level of the miRNA markers in comparison to the control expression level of the miRNA markers, the more severe the disease. Thus, a lesser decrease in the expression level of miRNA markers in comparison to control levels is indicative of stage I-II of endometriosis, e.g. a decrease in miRNA marker expression in the range of 10-30% in comparison to the expression level of miRNA marker controls. Greater decreases in miRNA marker expression levels in comparison to miRNA marker control expression levels (e.g. decreases of greater than about 50%) is indicative of more severe disease, i.e. stage III-IV endometriosis.

Disease progression may also be monitored using the present method to detect miRNA marker expression levels over time. If the marker expression levels do not change or increase over time, this indicates that the disease is not progressing. If marker expression levels are decreasing over time in comparison to control levels, this is indicative of disease progression.

Once a mammal has been diagnosed with endometriosis, the mammal can then be appropriately treated. In mild cases, the appropriate treatment may be administration of a pain medication, such as nonsteroidal anti-inflammatory drugs (NSAIDs), e.g. ibuprofen or naproxen, to address painful cramps. Alternatively, hormone therapy may be utilized to address the pain mild to moderate endometriosis, including, hormonal contraceptives (birth control pills, patches and vaginal rings); gonadotropin-releasing hormone (Gn-RH) agonists and antagonists to block the production of ovarian-stimulating hormones, lowering estrogen levels and preventing menstruation, optionally in combination with a low dose of estrogen or progestin to decrease menopausal side effects; progestin therapy, e.g. such as an intrauterine device (Mirena™), contraceptive implant or contraceptive injection (Depo-Provera™); and steroid treatment (e.g. danazol) to suppress the growth of the endometrium. For severe endometriosis, treatment by surgery is appropriate.

In another aspect, a method to monitor response by a mammal to treatment for endometriosis, including surgical or drug therapy (e.g. hormone therapy), is also provided. The method of monitoring a mammal following treatment of endometriosis comprises: determining the normalized expression level of selected miRNA markers in a sample from the mammal obtained prior to treatment (pre-treatment) and in a sample obtained following treatment (post-treatment). If the expression level of the miRNA markers in the pre-treatment sample shows a greater decrease in comparison to the expression level of the miRNA marker controls than the decrease of the miRNA marker expression level in the post-treatment sample in comparison to the miRNA marker control expression levels, this indicates that the mammal is responding to the treatment.

Disease recurrence may also be monitored in a mammal previously successfully treated for endometriosis using a method in accordance with the invention. A method as used to diagnose endometriosis in a first instance would be applicable.

In a further embodiment of the invention, a kit for use in detecting endometriosis is provided comprising reactants for the specific identification of selected miRNA markers, e.g. including specific PCR primers for at least 3 miRNA markers selected from the group of miR-199a-3p, miR-143-3p, miR-340-5p, let-7b-5p, miR-21-5p, miR-17-5p, miR-20a-5p and miR-103a-3p, and an miRNA reference marker selected from miR-148b-3p and hsa-miR-30e-5p. In preferred embodiments, the kit comprises primers for the miRNA markers, miR-17-5p, miR-20a-5p, miR-199a-3p, miR-143-3p, and let-7b-5p, or primers for the miRNA markers, miR-199a-3p, miR-143-3p, miR-340-5p, let-7b-5p, miR-21-5p, miR-17-5p, miR-20a-5p and miR-103a-3p, as well as primers for the miRNA reference markers, miR-148b-3p and miR-30e-5p.

The kit may be provided in the form of a biochip which incorporates the primers for the selected miRNA markers at pre-defined sites on a surface, e.g. bound to a suitable surface onto which sample may be applied and detection of target miRNA markers and reference markers may be detected. The primers may each be associated with an indicator such that in the presence of the targeted miRNA marker or reference marker, a detectable product or signal is released, as above. The biochip may be adapted for use with a blood sample, e.g. from a finger prick, or a menses sample.

In another embodiment, a biochip adapted for the electrochemical detection of circulating target miRNA markers is provided. miRNA marker-specific primers are bonded to circuits, e.g. an electrode, in a silicone microchip. When a target miRNA from a sample binds to its specific primer, it alters the voltage potential measured across the probe resulting in a measurable electrical output that is detectable by transducers in the device and which is proportional to the concentration of the miRNA marker in the sample.

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

The term "and/or" as used herein means that the listed items are present, or used, individually or in combination. In effect, this term means that "at least one of" or "one or more" of the listed items is used or present.

Embodiments of the invention are described by reference to the following Example(s) which are not to be construed as limiting.

Example 1

Next generation sequencing (NGS) is a well established method used for unbiased screening for the differential expression of genes and miRNA. Using NGS, a panel of 24 novel candidate miRNA were identified that were differentially expressed in plasma from women with surgically confirmed endometriosis compared to a population of women without surgical evidence of endometriosis. Quantitative real time-polymerase chain reaction (qRT-PCR) was used to validate differential expression of miRNA identified by NGS in a novel cohort of women with surgically confirmed endometriosis.

miRseq NGS of plasma samples on four pooled groups of samples collected during the early follicular phase as follows: 1) women (n=5) with Stage I-II endometriosis; 2) women (n=5) with Stage III-IV endometriosis; 3) women without endometriosis (controls, n=5); and 4) women without endometriosis but endometrial pathologies (e.g. adenomyosis, myomas, leiomyomas) (n=5). From this preliminary study, plasma levels of 69 candidate miRNAs were differentially expressed in women with endometriosis compared to the control group.

Results from NGS were subsequently validated using qRT-PCR to quantify novel candidate miRNA levels in 45 women with (n=30) or without (n=15) surgically confirmed endometriosis. Twenty miRNAs identified by NGS were differentially expressed (p 0.01 and 2 fold change) in cases vs. controls by qRT-PCR. Additional miRNAs were determined to be differentially expressed in endometrial tissue of women with endometriosis compared to controls and included to yield a final panel of 25 candidate miRNAs for further evaluation as shown in Table 1.

TABLE 1

List of candidate miRNA biomarkers and controls

| | # | miRNA ID | Assay Catalog # |
|---|---|---|---|
| miRNA markers of endometriosis evaluated in this study | 1 | hsa-miR-150-5p | YP00204660 |
| | 2 | hsa-miR-199a-3p | YP00204536 |
| | 3 | hsa-miR-143-3p | YP00205992 |
| | 4 | hsa-miR-199a-5p | YP00204494 |
| | 5 | hsa-miR-335-3p | YP00205613 |
| | 6 | hsa-miR-381-3p | YP00205887 |
| | 7 | hsa-miR-224-5p | YP00204641 |
| | 8 | hsa-miR-340-5p | YP00206068 |
| | 9 | hsa-let-7d-3p | YP00205627 |
| | 10 | hsa-miR-92a-3p | YP00204258 |
| | 11 | hsa-miR-221-3p | YP00204532 |
| | 12 | hsa-miR-486-5p | YP00204001 |
| | 13 | hsa-let-7b-5p | YP00204750 |
| | 14 | hsa-miR-122-5p | YP00205664 |
| | 15 | hsa-miR-21-5p | YP00204230 |
| | 16 | hsa-miR-133a-3p | YP00204788 |
| | 17 | hsa-miR-148a-5p | YP00204188 |
| | 18 | hsa-let-7a-3p | YP00206084 |
| | 19 | put-miR-5 | YCP0043333 |
| | 20 | put-miR-27 | YCP0043336 |
| | 21 | hsa-miR-125b-5p | YP00205713 |
| | 22 | hsa-miR-17-5p | YP00204771 |
| | 23 | hsa-miR-20a-5p | YP00204292 |
| | 24 | hsa-miR-3613-5p | YP02119046 |
| | 25 | hsa-miR-103a-3p | YP00204063 |
| Reference miRNA | 26 | hsa-miR-30e-5p | YP00204714 |
| | 27 | hsa-miR-148b-3p | YP00204047 |
| Extraction control | 28 | cel-miR-39-3p | YP00203952 |
| Template control | 29 | unisp3 | YP02119288 |
| | 30 | unisp6 | YP00203954 |

Example 2

Plasma samples from another unique cohort of women with surgically confirmed endometriosis (n=53) and disease-free controls (n=53) were collected for the validation study. Because lysis of red blood cells and even small amounts of hemolysis can confound results, plasma samples were checked for hemolysis using spectrophotometry. Absorbance results 0.2 indicated absence of hemolysis. In addition, as a further check for hemolysis, qRT-PCR was used to determine the ratio of miR-23a and miR-451. Cycle quantification 7.0 for miR-23a and miR-451 was considered to indicate lack of hemolysis, and samples having this Cq were included for candidate miRNA analysis.

miRNA signatures were quantified by qRT-PCR in hemolysis-free plasma samples of cases (n=25) and controls (n=28) using miRCURY LNA miRNA assay. Custom PCR panels were prepared and included candidate miRNA marker primers and miRNA reference primers for extraction, cDNA synthesis, and qPCR efficiency.

A group of three candidate reference miRNA with levels that were believed to be stable across all women with endometriosis and controls, namely, hsa-miR-103a-3p, hsa-miR-148b-3p and hsa-miR-30e-5p, were also found not to be influenced by the course of the menstrual cycle. By further checking expression differences between two groups for each of these candidate reference miRNAs, hsa-miR-103a-3p was found to be differentially expressed in women with endometriosis compared to the control group of women without endometriosis, and thus, was excluded as a control. Therefore, two miRNAs (hsa-miR-148b-3p and hsa-miR-30e-5p) were chosen as internal reference miRNA. Reference miRNAs with stable and equivalent plasma levels in women with endometriosis and controls were used to standardize/normalize circulating plasma miRNA results in which confounding from hemolysis was excluded.

Figure 1:
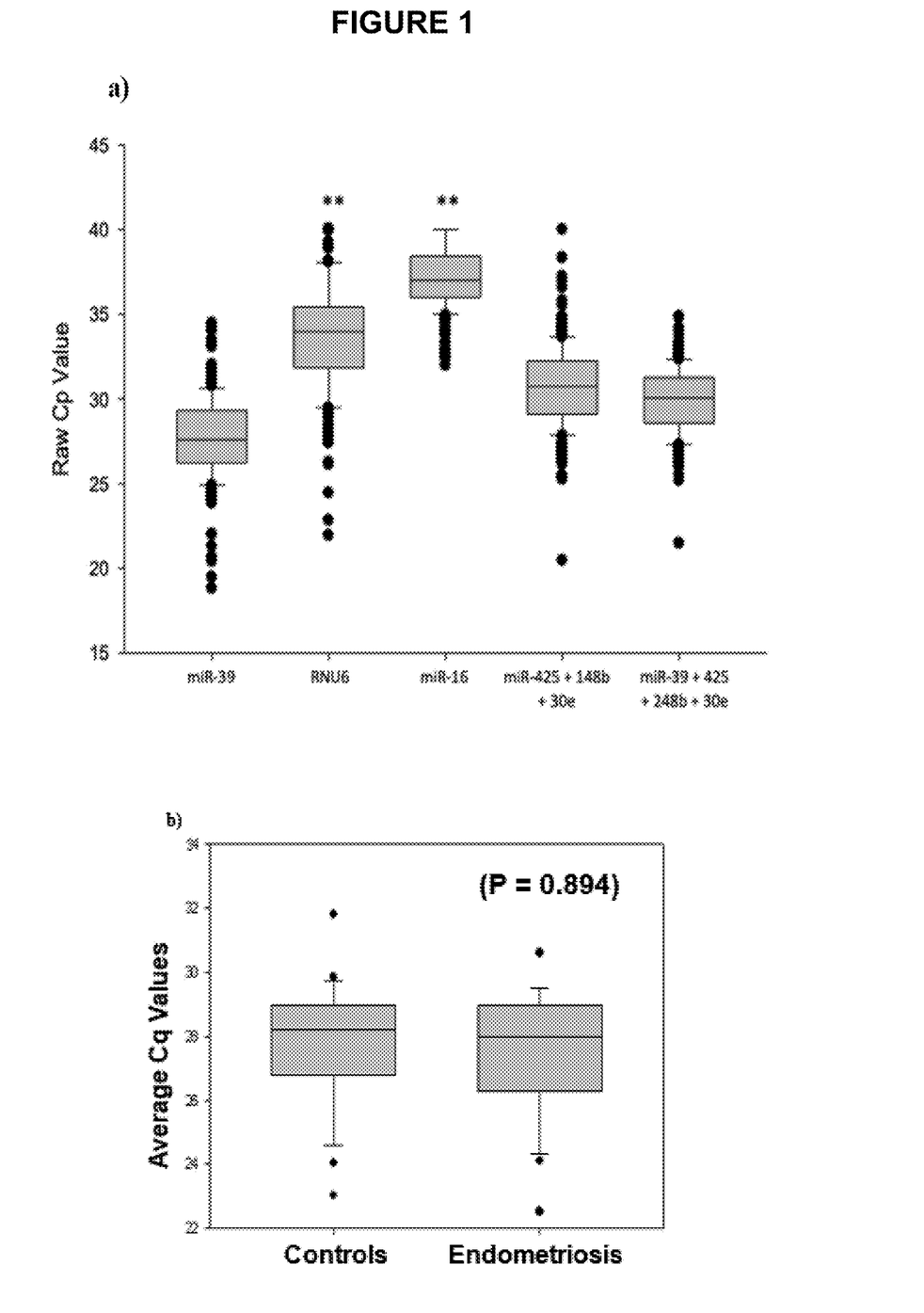
FIG. 1 shows a) box plots of the median crossing point (Cp) values with the 25th and 75th percentile for cel-miR-39 (used as an extraction control), RNU6 and miR-16, reference markers others have used to normalize miR results, and a panel of reference miRNA (hsa-miR-425, 148b, and 30e) alone and combined with cel-miR-39 (arrow). Whiskers depict the 5th and 95th percentiles. Data bars with ** were significantly different with p<0.001. The reference miRNAs (hsa-miR-425, 148b, and 30e) were stably expressed and more abundant than alternative reference miRNA (RNU6 or miR-16). hsa-miR-425, 148b, and 30e were stably expressed in women with and without endometriosis and used a reference miRNA to quantify differential expression of circulating miRNA. b) Circulating levels of reference miRNA used to standardize circulating levels of target miRNA were stably expressed in both women from the control group and in women with endometriosis. From analyses, hsa-miR-148b and 30e were the most reliable reference miRNA available to measure normalized circulating miRNA levels and therefore were selected to discriminate between women with endometriosis and controls in exemplary embodiments of the application.

FIG. 1 shows a comparison of the reference miRNA used to standardize circulating levels of target miRNA to discriminate between women with endometriosis and controls, using reference miRNA (has-miR-148-3p and has-miR-30e-5p) that expressed at equivalent levels in the plasma of women with surgically confirmed endometriosis and a control group of women without endometriosis. In FIG. 1a, box plots are shown to compare the median crossing point (Cp) values with the 25th and 75th percentile for cel-miR-39 (used as an extraction control), and different reference miRNA including RNU6 and miR-16 used by other investigators to normalize miR results, and reference miRNA (hsa-miR-425, 148b, and 30e) alone and combined with cel-miR-39 (arrow). Whiskers depict the 5th and 95th percentiles. Data bars with ** were significantly different with $p<0.001$. In comparison to reference miRNA used by other investigators (RNU6 and miR-16), reference miRNAs hsa-miR-425, 148b, and 30e were stably expressed and more abundant than alternative reference miRNA (RNU6 or miR-16). Therefore, hsa-miR-425,148b, and 30e were stably expressed in women with and without endometriosis and hsa-miR-148b and 30e as reference miRNA to quantify differential expression of circulating miRNA.

In FIG. 1b, circulating levels of reference miRNA used to standardize circulating levels of target miRNA were shown to be stably expressed in both women from the control group and in women with endometriosis. In particular, the mean Cq values for hsa-miR-148b-3p and hsa-miR-30e-5p showed no significant differences between women with endometriosis and the control group (p=0.894). The Cq value or cycle quantification value is the PCR cycle number at which the sample's reaction curve intersects the threshold line. This value expresses how many cycles it takes to detect a real signal from the sample. Real-Time PCR runs will have a reaction curve for each sample, and therefore many Cq values. The mean Cq value for the combination of hsa-miR-148b-3p, hsa-miR-30e-5p and hsa-miR-103a-3p was (p=0.838). However, the plasma levels of hsa-miR-103a-3p was significantly different between the two groups (p=0.007) when it was compared to three candidate reference gene average Cq values (including its own) or when it was compared to the other two candidate reference gene mean Cq values. Consequently, hsa-miR-103a-3p was excluded as a reference gene but included in all subsequent comparisons as a candidate marker of endometriosis. Furthermore, the mean Cq values of the two reference miRNAs (hsa-miR-148b-3p and hsa-miR-30e-5p) were used as reference miRNAs (in FIG. 1) to standardize miRNA results in women with endometriosis compared to the control group.

Figure 2:
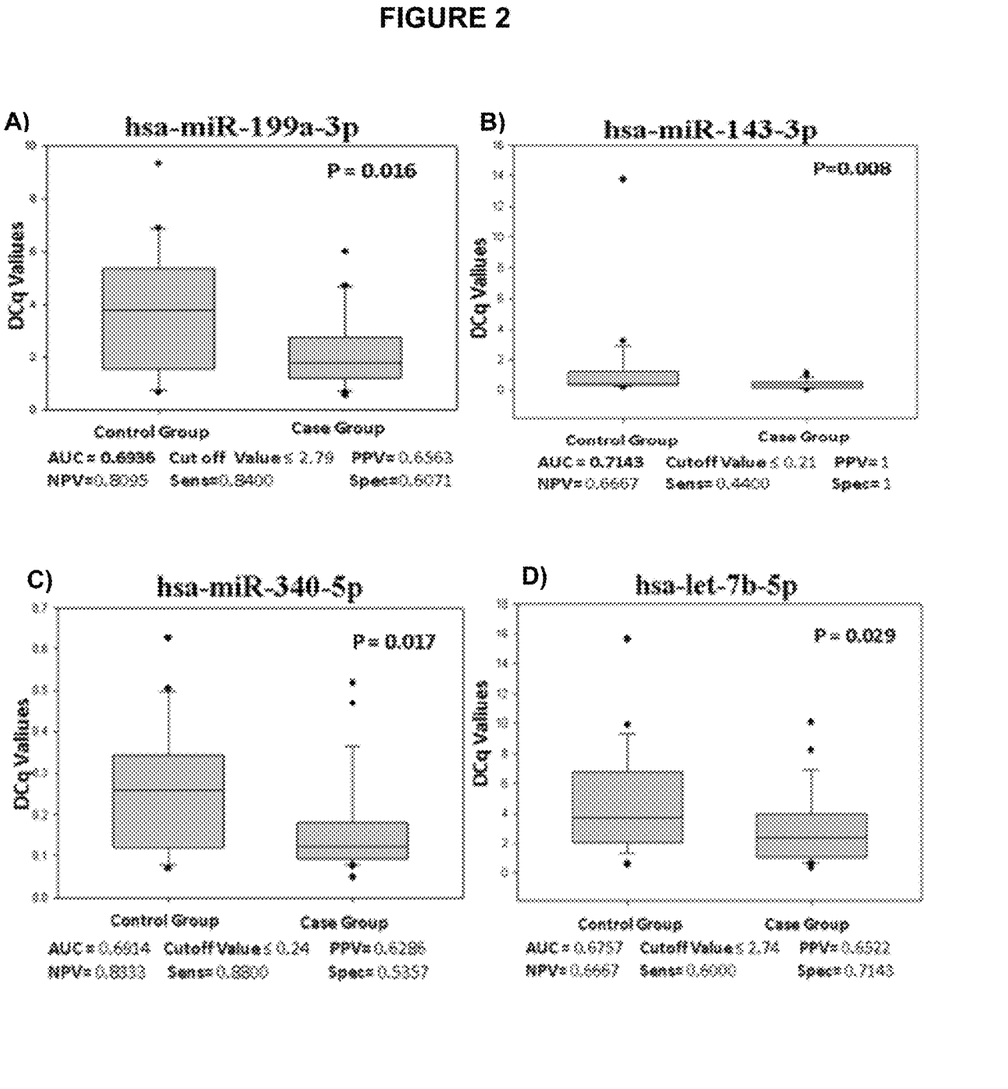
FIG. 2 shows the relative levels of eight different miRNA (A) has-miR-199-3p, B) has-miR-143-3p, C) has-miR-340-5p, D) has-let-7b-5p, E) has-miR-21-5p, F) has-miR-17-5p, F) has-miR-20a-5p, H) has-miR-103-3p) in the plasma of women with surgically confirmed endometriosis and a control group of women without endometriosis; the corresponding area under the curve (AUC), sensitivity, specificity, positive predictive value (PPV) and negative predictive value (NPV) are also depicted for each miRNA that was differently expressed in women with endometriosis compared to the control population.

Differences in miRNA expression between cases and controls was determined by the Mann-Whitney U test with a p value 0.05, considered significant. Circulating levels of eight miRNAs (miR-199a-3p, miR-143-3p, miR-340-5p, let-7b-5p, miR-21-5p, miR-17-5p, miR-20a-5p, miR-103a-3p) were determined to be significantly lower in cases compared to controls. FIG. 2 shows a comparison of the miRNA levels for each of the eight-target miRNA in this diagnostic panel) which were significantly different in women with endometriosis compared to control samples.

Figure 3:
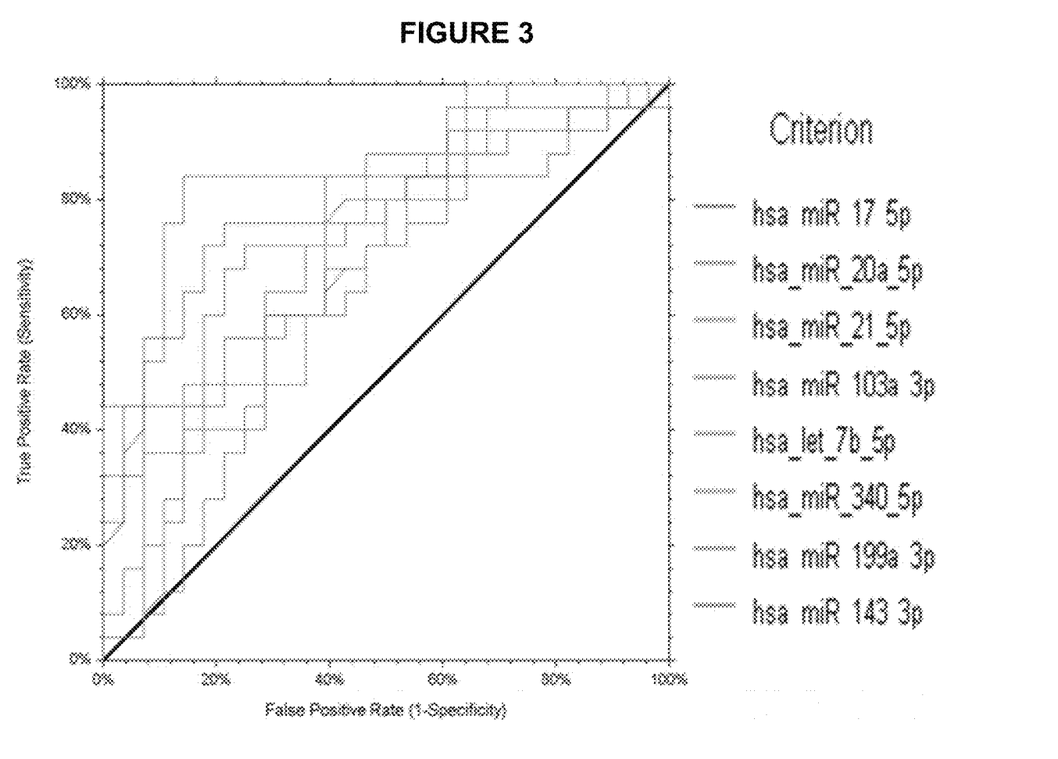
FIG. 3 shows the Receiver Operator Characteristic curve for each miRNA studied in exemplary embodiments of the application.

In order to define the diagnostic potential of each of the eight miRNAs with significantly different plasma levels, ROC curves were generated. FIG. 3 demonstrates a Receiver Operator Characteristic (ROC) for each of the eight-target miRNAs in the endometriosis diagnostic panel. The sensitivity and specificity for individual miRNAs (miR-199a-3p, 0.84 and 0.61; miR-143-3p, 0.44 and 1.00; miR-340-5p, 0.88 and 0.54; let-7b-5p, 0.60 and 0.71; miR-21-5p, 1.0 and 0.36; miR-17-5p, 0.84 and 0.86; miR-20a-5p, 0.76 and 0.76; and miR-103a-3p, 0.72 and 0.75) ranged between 0.44-1.00 and 0.36-1.00, respectively.

Figure 4:
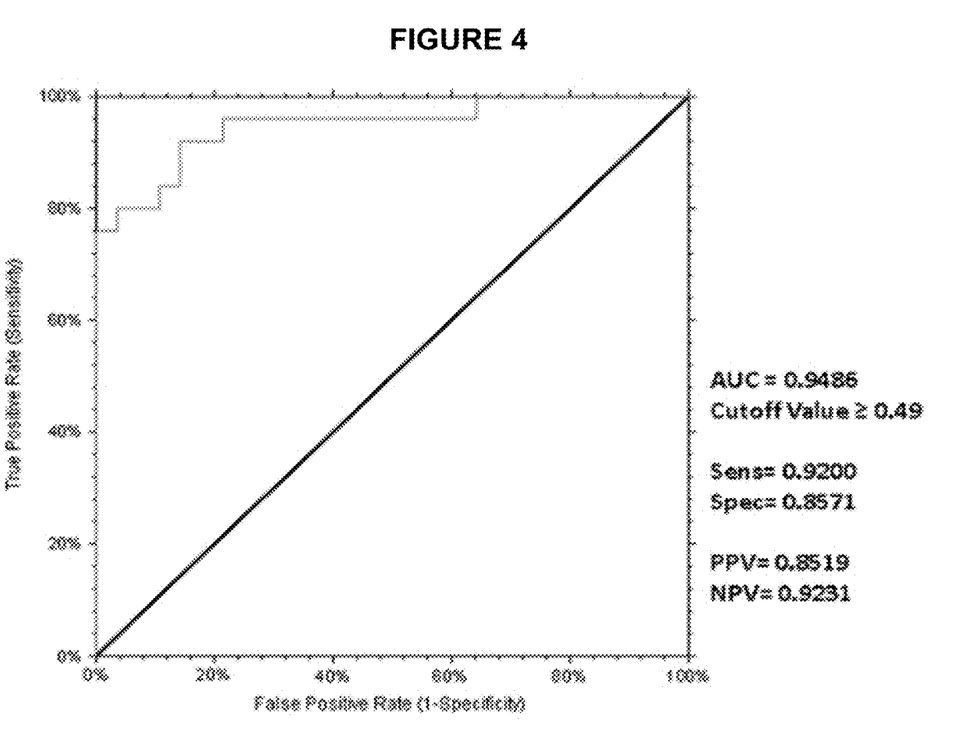
FIG. 4 shows the Receiver Operator Characteristic curves for the combination of the eight miRNA with circulating levels that were significantly different in women with endometriosis compared to controls in exemplary embodiments of the application.

Sensitivity and specificity, and PPV and NPV, of a panel including all 8 miRNAs, was determined. FIG. 4 shows the combined ROC for all eight-target miRNA in the diagnostic panel. Logistic regression of delta Cq values followed by ROC curve analysis for the eight miRNAs with plasma levels that differed between cases compared to controls produced AUC, optimal Youden Index, cut off, sensitivity, specificity, PPV and NPV for each combination. It was found that the combination of all eight miRNAs provided AUC of 0.9486, sensitivity and specificity of 0.92 and 0.86, with PPV and NPV of 0.85 and 0.92, respectively.

Figure 5:
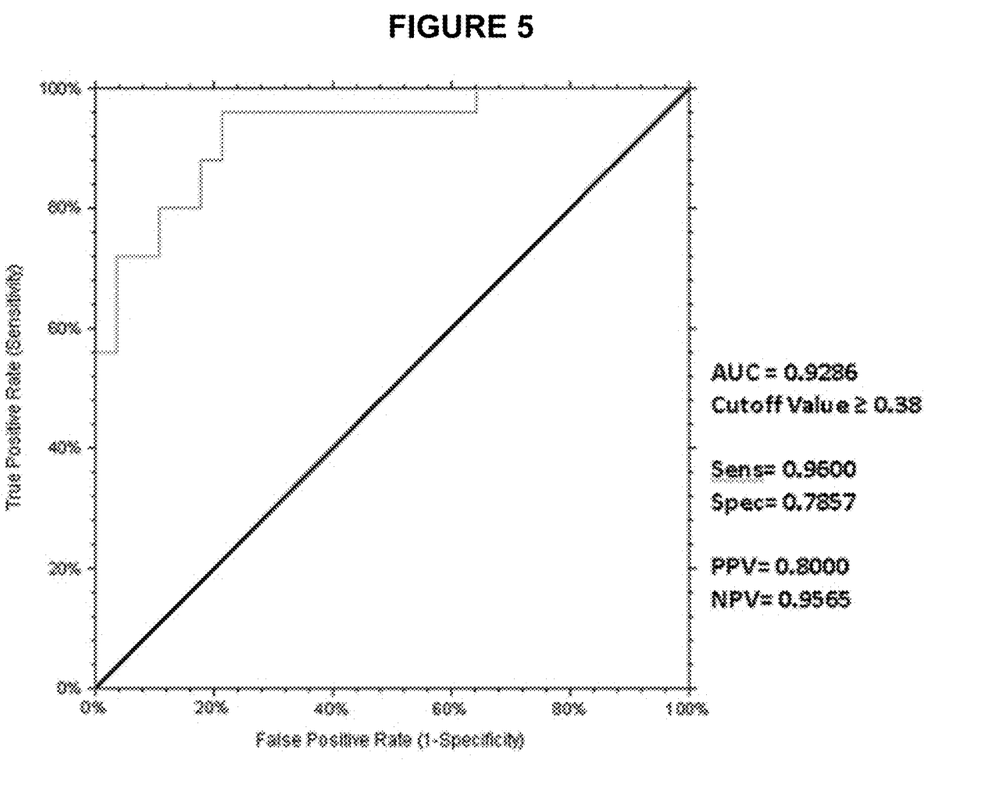
FIG. 5 shows the Receiver Operator Characteristic curves for the combination of the five miRNA with circulating levels that were significantly different in women with endometriosis compared to controls with sensitivity and specificity of 0.96 and 0.79, respectively, in exemplary embodiments of the application.

Narrowing the panel by combining five miRNAs (miR-17-5p, miR-20a-5p, miR-199a-3p, miR-143-3p, and let-7b-5p) produced produced an epigenetic signature with sensitivity and specificity of 0.96 and 0.79 with PPV and NPV values of 0.80 and 0.96, respectively. FIG. 5 shows the combined ROC for five-target miRNA in the diagnostic panel.

Therefore, several miRNAs were found to be differentially expressed in the plasma of women with endometriosis compared to a control population of women without endometriosis. Furthermore, the combination of five specific miRNAs identified in this application had sensitivity and specificity equivalent to laparoscopy in the diagnosis of endometriosis and can be used as a replacement test to diagnosis endometriosis, reducing the need for laparoscopy and mitigating surgical risk in this patient population.

While the present application has been described with reference to examples, it is to be understood that the scope of the claims should not be limited by the embodiments set forth in the examples but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

Agarwal S K, Chapron C, Giudice L C, Laufer M R, Leyland N, Missmer S A, Singh S S, and Taylor H S. Clinical diagnosis of endometriosis: a call to action. Am J Obstet Gynecol 2019: 220; 354.e351-354.e312.

Bartel D P. MicroRNAs: genomics, biogenesis, mechanism, and function. Cell 2004: 116; 281-297.

Bartel D P. MicroRNAs: target recognition and regulatory functions. cell 2009: 136; 215-233.

Bashti O, Noruzinia M, Garshasbi M, and Abtahi M. miR-31 and miR-145 as Potential Non-Invasive Regulatory Biomarkers in Patients with Endometriosis. Cell J 2018: 20; 293.

Bockaj M, Fung B, Tsoulis M, Foster W G, and Soleymani L. Method for Electrochemical Detection of Brain Derived Neurotrophic Factor (BDNF) in Plasma. Anal Chem 2018: 90; 8561-8566.

Burney R O and Giudice L C. Pathogenesis and pathophysiology of endometriosis. Fertility and sterility 2012: 98; 511-519.

Cho S, Mutlu L, Grechukhina O, and Taylor H S. Circulating microRNAs as potential biomarkers for endometriosis. Fertil Steril 2015: 103; 1252-1260 e1251.

Cosar E, Mamillapalli R, Ersoy G S, Cho S, Seifer B, and Taylor H S. Serum microRNAs as diagnostic markers of endometriosis: a comprehensive array-based analysis. Fertil Steril 2016.

Fadhlaoui A, Gillon T, Lebbi I, Bouquet de Jolinière J, and Feki A. Endometriosis and vesico-sphincteral disorders. Frontiers in surgery 2015: 2; 23.

Fassbender A, Burney R O, O D F, D'Hooghe T, and Giudice L. Update on Biomarkers for the Detection of Endometriosis. Biomed Res Int 2015: 2015; 130854.

Fuldeore M, Yang H, Du E X, Soliman A M, Wu E Q, and Winkel C. Healthcare utilization and costs in women diagnosed with endometriosis before and after diagnosis: a longitudinal analysis of claims databases. Fertility and sterility 2015: 103; 163-171. Giudice LC. Endometriosis. New England Journal of Medicine 2010: 362; 2389-2398.

Jia S-z, Yang Y, Lang J, Sun P, and Leng J. Plasma miR-17-5p, miR-20a and miR-22 are down-regulated in women with endometriosis. Human reproduction 2012: 28; 322-330.

Jia S Z, Yang Y, Lang J, Sun P, and Leng J. Plasma miR-17-5p, miR-20a and miR-22 are down-regulated in women with endometriosis. Hum. Reprod. 2013: 28; 322-330.

May K E, Conduit-Hulbert S A, Villar J, Kirtley S, Kennedy S H, and Becker C M. Peripheral biomarkers of endometriosis: a systematic review. Hum. Reprod. Update. 2010: 16; 651-674.

May K E, Villar J, Kirtley S, Kennedy S H, and Becker C M. Endometrial alterations in endometriosis: a systematic review of putative biomarkers. Hum. Reprod. Update. 2011: 17; 637-653.

Nisenblat V, Bossuyt P M, Shaikh R, Farquhar C, Jordan V, Scheffers C S, Mol B W, Johnson N, and Hull M L. Blood biomarkers for the non-invasive diagnosis of endometriosis. Cochrane Database Syst Rev 2016: 5; CD012179.

Nisenblat V, Sharkey D J, Wang Z, Evans S F, Healey M, Ohlsson Teague E M C, Print C G, Robertson S A, and Hull M L. Plasma microRNAs display limited potential as diagnostic tools for endometriosis. J Clin Endocrinol Metab 2019.

Nnoaham K E, Hummelshoj L, Webster P, d'Hooghe T, de Cicco Nardone F, de Cicco Nardone C, Jenkinson C, Kennedy S H, Zondervan K T, and Study WERFG. Impact of endometriosis on quality of life and work productivity: a multicenter study across ten countries. Fertility and sterility 2011: 96; 366-373. e368.

Nothnick W B, Falcone T, Joshi N, Fazleabas A T, and Graham A. Serum miR-451a Levels Are Significantly Elevated in Women With Endometriosis and Recapitulated in Baboons (Papio anubis) With Experimentally-Induced Disease. Reprod Sci 2017: 24; 1195-1202.

Rekker K, Saare M, Roost A M, Kaart T, Soritsa D, Karro H, Soritsa A, Simon C, Salumets A, and Peters M. Circulating miR-200-family micro-RNAs have altered plasma levels in patients with endometriosis and vary with blood collection time. Fertil Steril 2015: 104; 938-946 e932.

Rogers P A, Adamson G D, Al-Jefout M, Becker C M, D'Hooghe T$_M$, Dunselman G A, Fazleabas A, Giudice L C, Horne A W, Hull M L, et al. Research Priorities for Endometriosis. Reprod Sci 2017: 24; 202-226.

Shah D K, Correia K F, Vitonis A F, and Missmer S A. Body size and endometriosis: results from 20 years of follow-up within the Nurses' Health Study II prospective cohort. Hum. Reprod. 2013.

Sueta A, Yamamoto Y, Tomiguchi M, Takeshita T, Yamamoto-Ibusuki M, and Iwase H. Differential expression of exosomal miRNAs between breast cancer patients with and without recurrence. Oncotarget 2017: 8; 69934-69944.

Tamaresis J S, Irwin J C, Goldfien G A, Rabban J T, Burney R O, Nezhat C, DePaolo L V, and Giudice L C. Molecular classification of endometriosis and disease stage using high-dimensional genomic data. Endocrinology 2014: 155; 4986-4999.

Taylor H S, Adamson G D, Diamond M P, Goldstein S R, Horne A W, Missmer S A, Snabes M C, Surrey E, and Taylor R N. An evidence-based approach to assessing surgical versus clinical diagnosis of symptomatic endometriosis. Int J Gynaecol Obstet 2018: 142; 131-142.

Wang M, Gu H, Wang S, Qian H, Zhu W, Zhang L, Zhao C, Tao Y, and Xu W. Circulating miR-17-5p and miR-20a: molecular markers for gastric cancer. Molecular medicine reports 2012: 5; 1514-1520.

Wang W-T, Zhao Y-N, Han B-W, Hong S-J, and Chen Y-Q. Circulating microRNAs identified in a genome-wide serum microRNA expression analysis as noninvasive biomarkers for endometriosis. The Journal of Clinical Endocrinology & Metabolism 2013: 98; 281-289.

---

What is claimed is:

1. A method of detecting the expression level of miRNA markers in a biological sample obtained from a mammal comprising:
   i) detecting the expression level of at least 5 miRNA markers selected from the group of miR-199a-3p, miR-143-3p, miR-340-5p, let-7b-5p, miR-21-5p, miR-17-5p, miR-20a-5p and miR-103a-3p, in the biological sample; and
   ii) detecting the expression level of at least one miRNA reference marker selected from miR-148b-3p and miR-30e-5p in the biological sample.

2. The method of claim 1, wherein the mammal is a human female.

3. The method of claim 1, wherein the expression level of the miRNA markers and miRNA reference markers is determined using RT-PCR.

4. The method of claim 3, wherein the expression level of the miRNA reference marker, miR-148b 3p, is detected using a primer having the sequence, ucagugcaucacagaacuuugu (SEQ ID NO: 9), and the miRNA reference marker, miR-30e-5p, is detected using a primer having the sequence, uguaaacauccuugacuggaa (SEQ ID NO: 10).

5. The method of claim 1, wherein the expression level of both of the miRNA reference markers, miR-148b-3p and miR-30e-5p, is detected.

6. The method of claim 1, wherein the expression level of the at least 5 miRNA markers is detected using primers, wherein miR-340-5p is detected using the primer, uuauaaagcaaugagacugauu (SEQ ID NO: 1); let-7b-5p is detected using the primer, ugagguaguagguugugugguu (SEQ ID NO: 2); miR-21-5p is detected using the primer, uagcuuaucagacugauguuga (SEQ ID NO: 3); miR-17-5p is detected using the primer, caaagugcuuacagugcagguag (SEQ ID NO: 4); miR-20a-5p is detected using the primer, uaaagugcuuauagugcagguag (SEQ ID NO: 5); miR-103a-3p is detected using the primer, agcagcauuguacagggcuauga (SEQ ID NO: 6); miR-199a-3p is detected using the primer, acaguagucugcacauugguua (SEQ ID NO: 7); and miR-143-3p is detected using the primer, ugagaugaagcacuguagcuc (SEQ ID NO: 8).

7. The method according to claim 1, wherein the miRNA markers comprise miR-199a-3p, miR-143-3p, miR-340-5p, let-7b-5p, miR-21-5p, miR-17-5p, miR-20a-5p and miR-103a-3p.

8. The method according to claim 1, wherein the miRNA markers comprise miR-17-5p, miR-20a-5p, miR-199a-3p, miR-143-3p, and let-7b-5p.

9. A method of diagnosing and treating endometriosis in a mammal comprising:
   i) detecting the expression level of at least 5 miRNA markers selected from the group of miR-199a-3p, miR-143-3p, miR-340-5p, let-7b-5p, miR-21-5p, miR-17-5p, miR-20a-5p and miR-103a-3p, in a biological sample obtained from the mammal;
   ii) detecting the expression level of an miRNA reference marker selected from miR-148b-3p and miR-30e-5p in the biological sample obtained from the mammal;
   iii) normalizing the expression level of the miRNA markers based on the expression level of the miRNA reference marker in the sample and in a control; and iv) treating the mammal in which the normalized expression levels of the miRNA markers are less than the expression level of the miRNA markers in the control with a treatment selected from hormone therapy, gonadotropin-releasing hormone (Gn-RH) agonists, Gn-RH antagonists and steroid treatment.

10. The method of claim 9, wherein the control is obtained from mammals that do not have endometriosis.

11. The method according to claim 9, wherein the miRNA markers comprise miR-199a-3p, miR-143-3p, miR-340-5p, let-7b-5p, miR-21-5p, miR-17-5p, miR-20a-5p and miR-103a-3p.

12. The method according to claim 9, wherein the miRNA markers comprise miR-17-5p, miR-20a-5p, miR-199a-3p, miR-143-3p, and let-7b-5p.

13. The method according to claim 9, wherein the expression level of both miRNA reference markers, miR-148b-3p and miR-30e-5p, is detected.

14. The method according to 9, wherein the biological sample is selected from the group consisting of blood, serum, plasma, urine, peritoneal fluid, uterine fluid and endometrial tissue.

15. The method of claim 9, wherein the expression level of the miRNA markers and miRNA reference markers is determined using RT-PCR.

16. The method of claim 9, wherein the expression level of the miRNA reference marker, miR-148b-3p, is detected using a primer having the sequence, ucagugcaucacagaacuuugu (SEQ ID NO: 9), and the miRNA reference marker, miR-30e-5p, is detected using a primer having the sequence, uguaaacauccuugacuggaa (SEQ ID NO: 10).

17. The method of claim 9, wherein the expression level of the at least 5 miRNA markers is detected using primers, wherein miR-340-5p is detected using the primer, uuauaaagcaaugagacugauu (SEQ ID NO: 1); let-7b-5p is detected using the primer, ugagguaguagguugugugguu (SEQ ID NO: 2); miR-21-5p is detected using the primer, uagcuuaucagacugauguuga (SEQ ID NO: 3); miR-17-5p is detected using the primer, caaagugcuuacagugcagguag (SEQ ID NO: 4); miR-20a-5p is detected using the primer, uaaagugcuuauagugcagguag (SEQ ID NO: 5); miR-103a-3p is detected using the primer, agcagcauuguacagggcuauga (SEQ ID NO: 6); miR-199a-3p is detected using the primer, acaguagucugcacauugguua (SEQ ID NO: 7); and miR-143-3p is detected using the primer, ugagaugaagcacuguagcuc (SEQ ID NO: 8).

* * * * *